United States Patent [19]

Link et al.

[11] Patent Number: 5,635,347

[45] Date of Patent: Jun. 3, 1997

[54] RAPID ASSAYS FOR AMPLIFICATION PRODUCTS

[75] Inventors: John R. Link, Springfield, Va.; Satyanarayana R. Gudibande, Rockville; John H. Kenten, Gaithersburg, both of Md.

[73] Assignee: IGEN, Inc., Gaithersburg, Md.

[21] Appl. No.: 188,943

[22] Filed: Jan. 28, 1994

Related U.S. Application Data

[63] Continuation of Ser. No. 792,602, Nov. 15, 1991, abandoned, which is a continuation-in-part of Ser. No. 652,427, Feb. 6, 1991, abandoned, which is a continuation-in-part of Ser. No. 539,389, Jun. 18, 1990, abandoned, which is a continuation of Ser. No. 266,882, Nov. 3, 1988, abandoned, which is a continuation-in-part of Ser. No. 117,017, Nov. 4, 1987, abandoned, which is a continuation-in-part of Ser. No. 858,354, Apr. 30, 1986, abandoned.

[51] Int. Cl.$^6$ .............. C12Q 1/68; C12P 19/34; C07H 21/04
[52] U.S. Cl. .............. 435/6; 435/91.2; 435/91.5; 536/24.3; 436/164; 436/172; 935/8; 935/17; 935/77; 935/78
[58] Field of Search .............. 435/6, 91.2, 91.5; 935/77, 78, 8, 17; 436/164, 172; 536/24.13

[56] References Cited

U.S. PATENT DOCUMENTS

| 4,683,195 | 7/1987 | Mullis | 435/6 |
| 4,683,202 | 7/1987 | Mullis | 435/91 |
| 5,210,015 | 5/1993 | Gelfand | 435/6 |

FOREIGN PATENT DOCUMENTS

| A-33343/89 | 11/1989 | Australia. |
| 0297379 | 1/1989 | European Pat. Off.. |
| WO87/06706 | 11/1987 | WIPO. |

OTHER PUBLICATIONS

Kuman et al, Technique (1990) 2:101–108.
Boehringer Mannheim Catalog, 1990/1991, p. 63.
Chehab et al Proc Nat Acad Sci USA (1989) 86: 9178–9182.
Nelson et al (Nucleic Acid Res) 198 9:17:7187–7194.
Kenten et al Clin Chem (1991) 37:1626–1632.
Erhan and Greller, *Nature*, vol. 251, p. 353 (1974).
Newman, A.R., *Analytical Chemistry* (1990) 62:1063A–1065A.
Urdea, M.S., et al., *Nucleic Acids Res.* (1988) 16:4937–56.
Arnold, L.J., et al., *Clin. Chem.* (1989) 35:1588–94.
Beck, S., et al., *Nucleic Acids Res.* (1989) 17;5115–5123.
Ou C–Y, et al., *Science* (1988) 239:295–97.
Prior, T.W., et al. *Clin. Chem.* (1990) 36:1756–59.
Kenten, J.H., et al. *Clin. Chem.* (1991) 37:1626–32.
Nelson, P., et al., *Nucleic Acids Res.* (1989) 17:7187.
Blackburn, G.F., et al., *Clin. Chem.* (1991) 37:1534–39.

*Primary Examiner*—Carla J. Meyers
*Attorney, Agent, or Firm*—Curtis, Morris & Safford, P.C.

[57] ABSTRACT

A method of detecting a nucleic acid sequence of interest in the amplification product of a polymerase chain reaction or other primer directed reaction comprising the steps of:

(a) incorporating in a polymerase chain reaction mixture or other primer directed reaction mixture at least one nucleic acid sequence complementary to said nucleic acid sequence of interest labeled (i) at the 3' end thereof, or (ii) at the 3' and the 5' end thereof with a compound capable of electrochemiluminescence;

(b) conducting a polymerase chain reaction or other primer directed reaction; and (c) measuring the electrochemiluminescence of labeled amplification product.

7 Claims, 3 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
    ( A ) LENGTH: 4 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

A T G C                                                                                    4

( 2 ) INFORMATION FOR SEQ ID NO:2:

( i ) SEQUENCE CHARACTERISTICS:
    ( A ) LENGTH: 4 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

G C A T                                                                                    4

( 2 ) INFORMATION FOR SEQ ID NO:3:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

ATAATCCACC TATCCCAGTA GGAGAAAT                                                             28

( 2 ) INFORMATION FOR SEQ ID NO:4:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

TTTGGTCCTT GTCTTATGTC CAGAATGC                                                             28

( 2 ) INFORMATION FOR SEQ ID NO:5:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

ATCCTGGGAT TAAATAAAAT AGTAAGAATG TATAGCCCTA C 41

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GACTTCACTT CTAATGATGA 20

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CTCTTCTAGT TGGCATGCT 19

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GAAACACCAA AGATGATATT 20

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AACACCAATG ATATTTCTT T 21

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GAAAATGTGC TGACCGGACA TGAAAATGAG 30

( 2 ) INFORMATION FOR SEQ ID NO:11:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
GACTTCACTT  CTAATGATGA  TAAAGAAAAT  ATCATCTTTG  GTGTTTCCTA  TGATGAATAT       60

AGATACAGAA  GCGAGCATGC  CAACTAGAAG  AG                                      92
```

( 2 ) INFORMATION FOR SEQ ID NO:12:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
GACTTCACTT  CTAATGATGA  TAAAGAAAAT  ATCATTGGTG  TTTCCTATGA  TGAATATAGA       60

TACAGAAGCG  AGCATGCCAA  CTAGAAGAG                                           89
```

RAPID ASSAYS FOR AMPLIFICATION PRODUCTS

This application is a continuation of application Ser. No. 07/792,602, filed Nov. 15, 1991, now abandoned, and is a continuation-in-part of application Ser. No. 07/652,427, filed Feb. 6, 1991, now abandoned, which was a continuation-in-part of application Ser. No. 07/539,389, filed Jun. 18, 1990, now abandoned, which in turn was a continuation of application Ser. No. 07/266,882, filed Nov. 3, 1988, now abandoned, which was a continuation-in-part of application Ser. No. 07/117,017, filed Nov. 4, 1987, now abandoned, which was a continuation-in-part of application Ser. No. 858,354, filed Apr. 30, 1986, now abandoned. Each of the above-mentioned U.S. applications is hereby incorporated herein by reference.

FIELD OF THE INVENTION

This invention relates to the detection or quantitation of amplified nucleic acid sequences. More specifically, this invention relates to the detection or quantitation of nucleic acid analytes of interest in the amplification product of a polymerase chain reaction in rapid, one step, homogeneous assays.

Several publications are referenced in this application by arabic numerals in parenthesis. Full citation of these references is found at the end of the specification immediately preceding the claims. These references describe the state-of-the-art to which this invention pertains.

BACKGROUND OF THE INVENTION

The use of nucleic acid hybridization methods to detect disease states and infectious agents is a rapidly emerging technology (1). These methods have largely involved simple nonradioactive formats, aimed at achieving acceptance in the clinical laboratory (2,3). These assays use chemiluminescent or enzyme labels, or combinations of these to obtain the desired sensitivity (4). The rapid sample preparation offered by PCR offers the possibility of developing rapid and simple assays.

Nucleic Acid Amplification Processes

It is well known that a nucleic acid such as deoxyribonucleic acid (DNA) is able to serve as its own template during self-replication. It is also well known that a double stranded or duplex nucleic acid can be separated into its component single strands. These properties have been exploited to permit the in vitro amplification and modification of nucleic acid sequences by the polymerase chain reaction (PCR).

PCR is an in vitro, enzyme-based replication of nucleic acid sequences, using two oligonucleotide primers designed to hybridize to opposite strands and flank the region of interest on the target polynucleotide sequence. During repetitive cycles the nucleic acid is subjected to strand separation, typically by thermal denaturation, the primers are hybridized (by annealing if thermal cycling is used) to the single strand templates, and an enzyme such as DNA polymerase (DNA template to DNA primer extension) or reverse transcriptase (ribonucleic acid or "RNA" template to DNA primer extension or DNA template to DNA primer extension) extends the primers on the templates. Both of the strands (plus and minus), including newly synthesized strands are made available as templates for the extension of both primers respectively by the strand separation step. The result, with two primers, is an exponential increase (hence the term "chain reaction") in template nucleic acid copy number (both plus and minus strands) with each cycle, because with each cycle both the plus and minus chains are replicated. The nucleic acid duplex which results will have termini corresponding to the ends of the specific primers used. It is possible, by means of PCR, to amplify, detect, or otherwise modify a nucleic acid sequence in vitro.

The preparation of primers for PCR requires that the terminal sequences of the nucleic acid strands (both the plus and minus templates) to be amplified or detected, be known (5). The sequence information may be derived by direct sequencing of the terminals of the nucleic acid of interest, or by sequencing the terminal of a polypeptide and producing a corresponding copy oligonucleotide primer. The optimal primer size is typically about 20–30 bases in length, but workable primers may be smaller or larger in particular circumstances. As is well known, as primer size decreases, the likelihood that the primer will hybridize to an unplanned site on the sequence of interest increases. Unplanned hybridizations can lead to an interruption of amplification of the desired product and production of products having either a smaller size or an undesired primer insert. Thus, the selection of two optimal primers for PCR requires the avoidance of unplanned hybridization with the sequence of interest whenever practical.

The rational selection of primer sequence to avoid unplanned hybridizations is well known. Algorithms are known by which the artisan may compare proposed primer sequences to the entire template sequence (where known) and to any other sequences which are known to be present in an assay mixture.

The necessity for determining the terminal portion of the opposite strands of a nucleic acid sequence of interest and preparing two primers hybridizable thereto may be avoided by means of a universal primer. All DNA sequences present will receive a universal primer binding site and be amplified by the universal primer.

PCR amplification has been used to isolate new gene sequences from a polynucleotide sequence library. While new genes may also be isolated by means of a sufficiently complementary probe incorporating a portion of the sequence of the new gene, such probe isolation methods lack the sensitivity provided by PCR.

In the prior art assays based upon PCR, nucleic acid probes labeled at their 5' end have been used to hybridize to the nucleic acid analytes of interest. These probes occasionally enter into the polymerase chain reaction at their unlabeled 3' end resulting in spurious results. The prior art assays are also heterogeneous, i.e. separation assays. As such they are time consuming and the multiple wash steps involved introduce the possibility of contamination of the assay sample.

Detection of Labeled Nucleic Acid Sequence

Numerous methods and systems have been developed for the detection and quantitation of nucleic acid analytes of interest in biochemical and biological substances. Typically, the existence of a nucleic acid analyte of interest is indicated by the presence or absence of an observable "label" attached to a probe which binds to the analyte of interest. Of particular interest are labels which can be made to luminesce through photochemical, chemical, and electrochemical means.

"Photoluminescence" is the process whereby a material is induced to luminesce when it absorbs electromagnetic radiation. Fluorescence and phosphorescence are types of photoluminescence. "Chemiluminescent" processes entail the creation of luminescent species by chemical transfer of energy. "Electrochemiluminescence" entails creation of luminescent species electrochemically.

Electrochemiluminescent (ECL) assay techniques are an improvement on chemiluminescent techniques. They provide a sensitive and precise measurement of the presence and concentration of an analyte of interest. In such techniques, the incubated sample is exposed to a voltametric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such ECL techniques, reference is made to PCT published application U.S. Ser. No. 85/02153 (W086/02734), PCT published application U.S. Ser. No. 87/00987 (W087/06706) and PCT published application U.S. Ser. No. 88/03947 (W089/04302). The disclosures of the aforesaid applications are incorporated by reference.

It is possible to carry out electrochemiluminescent assays with and without a separation step during the assay procedure, and to maximize the signal modulation at different concentrations of analyte so that precise and sensitive measurements can be made.

PCT published application number U.S. Ser. No. 89/04919 (W090/05301) teaches sensitive, specific binding assay methods based on a luminescent phenomenon wherein inert microparticulate matter is specifically bound to one of the binding reactants of the assay system. The assays may be performed in a heterogeneous (one or more separation steps) assay format and may also be used most advantageously in a homogeneous (nonseparation) assay format.

The luminescence arises from electrochemiluminescence (ECL) induced by exposing the label compound, whether bound or unbound to specific binding partners, to a voltametric working electrode. The ECL reactive mixture is controllably triggered to emit light by a voltage impressed on the working electrode at a particular time and in a particular manner to generate light.

U.S. patent application Ser. No. 267,509, now abandoned, and U.S. patent application Ser. No. 266,914, now abandoned, relate to preferred assay compositions. The disclosures of these applications are incorporate by reference.

U.S. patent application Ser. No. 267,234, now U.S. Pat. No. 5,061,445 and U.S. patent application Ser. No. 744,890, now U.S. Pat. No. 5,247,243 teach preferred apparatus for the conduct of ECL-based assays. U.S. patent application Ser. No. 652,427 describes preferred methods and apparatus for conducting ECL-based assays. The disclosures of all these applications, which are also incorporated by reference, permit the detection and quantitation of extremely small quantities of analytes in a variety of assays performed in research and clinical settings.

OBJECTS OF THE INVENTION

It is a primary object of the invention to provide a method for rapidly conducting assays for nucleic acids amplified in polymerase chain reactions or other primer directed amplifications.

It is another and related object of the invention to provide a method for rapidly conducting sensitive, reliable homogeneous assays for nucleic acids of interest amplified in polymerase chain reactions.

It is yet another and related object of the invention to provide such assays which avoid the wash steps and sample contamination associated with prior art assays.

It is a further and related object of the invention to provide assays which avoid the problems and spurious results associated with the use of 5' probes.

SUMMARY OF THE INVENTION

These objects are achieved in rapid non-separation assays for amplified DNA which avoid the contamination and time wasted by the addition of probe and the multiple wash steps used in conventional assays. Oligonucleotide primers, bound to a binding moiety or detectable label and an oligonucleotide probe, labeled at its 3' or 3' and 5' ends with either a binding moiety or detectable label, such that both a binding moiety and a detectable label are both present in the mixture of primer and probe. This mixture of probe and primer is introduced into a PCR or other primer directed reaction mixture, such that the mixture is complete for reaction on the addition of the modified primer. The 3' or 3'5' labeled probes are not incorporated into the PCR product and thus maintain their specificity for hybridization unlike 5' labeled primers. Samples from these PCR/hybridizations are then sampled into a suspension of streptavidin beads and placed directly in an ECL analyzer. This rapid sample handling avoids the wash steps involved with typical hybridization assays.

DETAILED DESCRIPTION OF THE INVENTION

Definitions

Figure 1:
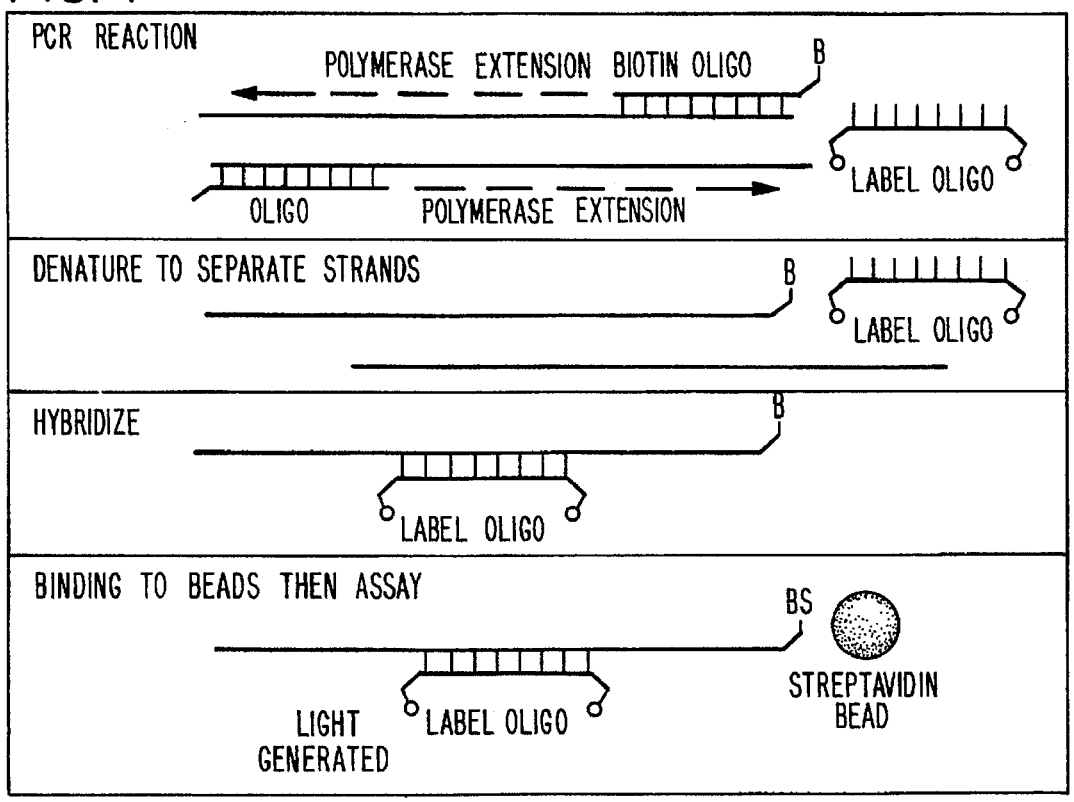
FIG. 1 is an assay format for rapid one step assay.

In order to more clearly understand the invention, certain terms are defined as follows.

A "nucleotide" is one of four bases: adenine, cytosine, guanine, and thymine (DNA) or uracil (RNA), plus a sugar (deoxyribose for DNA, ribose for RNA), plus a phosphate. In order to provide monomers for the DNA polymerization reaction, typically all four of the deoxynucleotide triphosphates are required. A nucleotide as defined herein may also include modified bases such as 5-methyl-dCTP and 7-deaza-dGTP used to improve the action of polymerase on templates. The term nucleotide as used herein also includes bases linked to biotin and digoxigenin (Digoxigenin-11-UTP from Boehringer Mannheim, Indianapolis, Ind.), and biotin-21-UTP and amino-7-dUTP (Clontech, Palo Alto, Calif.) which may be incorporated directly into a primer or into a primer extension product during amplification, to provide for selective binding of amplified sequences.

An "oligonucleotide" is a sequence formed of at least two nucleotides. A "polynucleotide" is a long oligonucleotide and may be either RNA or DNA. While the term oligonucleotide is generally used in the art to denote smaller nucleic acid chains, and "polynucleotide" is generally used in the art to denote larger nucleic acid chains including DNA or RNA chromosomes or fragments thereof, the use of one or the other term herein is not a limitation or description of size unless expressly stated to be.

The term "nucleic acid" refers to a polynucleotide of any length, including DNA or RNA chromosomes or fragments thereof with or without modified bases as described above.

A "sequence" (e.g. sequence, genetic sequence, polynucleotide sequence, nucleic acid sequence) refers to the actual enumerated bases (ribose or deoxyribose) present in a polynucleotide strand reading from the 5' to 3' direction.

The "complement" to a first nucleotide sequence is well known to be a second sequence comprising those bases which will pair by Watson-Crick hybridization with the first sequence. Thus, the complement to the deoxyribonucleic acid (DNA) sequence 5'-ATGC 3' (SEQ ID NO: 1) is well known to be 5'-GCAT 3'(SEQ ID NO: 2). For duplex, or double stranded DNA, each of the two strands are described as complementary to the other or as a complementary pair. The terms complement and anticomplement may also be used. With reference to the identification of the strand of duplex DNA from which transcription to RNA proceeds, the transcription strand is generally described as plus and its complement as minus (or "+" and "−"), or the transcription strand may be described as the sense strand, and its complement as antisense. Two strands each hybridized to the other having all base pairs complementary, are 100% complementary to each other. Two strands, each hybridized to the other, having 5% of bases non-complementary, are 95% complementary (or the two strands have 95% complementarily).

"Homology" between polynucleotide sequences refers to the degree of sequence similarity between the respective sequences. Two strands which are identical in sequence have 100% sequence homology. Two strands which differ by 5% of sequences have 95% sequence homology. The greater the degree of homology between two strands A and B, the greater the complementarity between A and the complement of B.

A "probe" is a single or double stranded nucleic acid which has a sequence complementary to a target nucleic acid sequence of interest and which has some additional feature enabling the measurement of the probe-target duplex. The artisan will understand that if the probe and/or the target is double stranded, the double stranded nucleic acid must undergo strand separation before hybridization can take place.

A probe is rendered detectable by an attached tag or label. A tag or label linked to a probe may include, in principle, a fluorescent or luminescent tag, an isotopic (e.g. radioisotope or magnetic resonance) label, a dye label, an enzyme label, an antigenic determinant detectable by an antibody, or a binding moiety such as biotin enabling yet another moiety such as a streptavidin coated bead to specifically attach to the probe. When the labeled or tagged probe-target duplex is formed, that duplex may be detected by the characteristic properties of the tag or label. The probe with its label moiety is captured by the target with its labeled moiety via hybridization and duplex formation allowing detection by a label.

A "primer" is a relatively short segment of oligonucleotide which is complementary to a portion of the sequence of interest (the sequence of interest can be a subfragment within a larger nucleic acid sequence). A primer represents a 5' terminus of the resulting extension product. A primer which is complementary at its 3' terminus to the sequence of interest on the template strand enables this 3' terminus to be acted on by a polymerase on hybridization to the template. A primer may also be modified at its 5' end with a binding moiety or detectable label.

"Strand separation" refers to the conversion of a double stranded or duplex nucleic acid to two complementary single stranded polynucleotides. The separation process may employ well known techniques including: enzyme mediated separation (e.g. by the enzyme helicase (5), physical-chemical separation (pH, ionic concentration and the like), and thermal separation also known as thermal denaturing. Thermal denaturing (also referred to as "melting") is the separation of a double stranded polynucleotide (fully or partially duplex) into at least two single strands of polynucleotide by raising the temperature of the solution holding that polynucleotide.

"Hybridization" describes the formation of double stranded or duplex nucleic acid from complementary single stranded nucleic acids. Hybridization may take place between sufficiently complementary single stranded DNA and/or RNA to form: DNA-DNA, DNA-RNA, or RNA-RNA.

The in vitro amplification of DNA is catalyzed by DNA polymerase. A number of types of DNA polymerase are known to the art. They generally share the common property of catalyzing the synthesis of a double stranded DNA sequence utilizing a single stranded template to which a primer is annealed. DNA polymerases extracted from most organisms become inactive at the temperatures required for thermal denaturing of nucleic acids. Thus, replacement of the enzyme at the start of each thermal cycle, or the addition of a factor able to prevent heat inactivation, is required if such heat sensitive enzymes are utilized. The DNA polymerases which are preferred for in vitro PCR as well as for the invention are derived from organisms which thrive at high temperatures and thus are heat resistant, i.e. thus maintain adequate catalytic activity at the temperature which denatures duplex DNA.

The reaction catalyzed by DNA polymerase is known to the art, and referred to herein as the "DNA polymerase reaction". The reaction requires some or all of the four deoxyribonucleotide triphosphates, primers, preferably in molar excess and a means for cyclic strand separation. Strand separation is preferably achieved by thermal cycling between annealing and denaturation temperatures. Reverse transcriptase is known to mediate both RNA to DNA copying, as well as DNA to DNA copying. Hence, any number of enzymes now known will catalyze the chain reaction.

"Electrochemiluminescent (ECL) labels" are those which can be made to become luminescent species when acted on electrochemically. Such ECL labels are described in PCT published applications by Bard et al. and Massey et al. (PCT US85/02153, WO86/02734 and PCT US87/00987, WO87/06706).

The terms "detection" and "quantitation" are referred to as "measurement", it being understood that quantitation may require preparation of reference compositions and calibrations.

"ECL apparatus" an "ECL analyzer" is any apparatus for performing electrochemiluminescence based assays.

DETAILED DESCRIPTION

Improved rapid, non-separation assays for amplified nucleic acid sequences have been developed using oligonucleotides having 3' or 3'5' electrochemiluminescent labels. Oligonucleotides having 3' or 3'5' labels are not able to act as primers in the PCR or other primer directed reactions. They remain at the end of the amplification process available for hybridization to the excess of amplified nucleic acid.

Assays making use of this probe system are rapid because the probe can hybridize within the thermocycler program. By using ECL technology to detect binding events the need for external washes or other manipulations is avoided. Of course, wash steps may optionally be used. These assay formats obviate the need to make separate additions and to risk contamination problems. While described below primarily in connection with PCR reactions, the invention can be used in any primer directed reaction.

Assays for the detection of the HIV1 gag gene and the human cystic fibrosis gene based on the use of previously described PCR protocols (6,7) is described below. Also described is a study of 15 patient samples tested for their cystic fibrosis status. Samples used were 5 normal, 5 heterozygous for the 508 deletion, and 5 homozygous for the 508 deletion.

In its preferred embodiment the invention comprises a method of detecting a nucleic acid sequence of interest in the product of a polymerase chain reaction or other primer directed amplification reaction comprising the steps of (a) incorporating in a polymerase chain reaction or other primer directed reaction mixture, at least one labeled nucleic acid sequence which is capable of electrochemiluminescence and is complementary to said nucleic acid sequence of interest, having the formula:

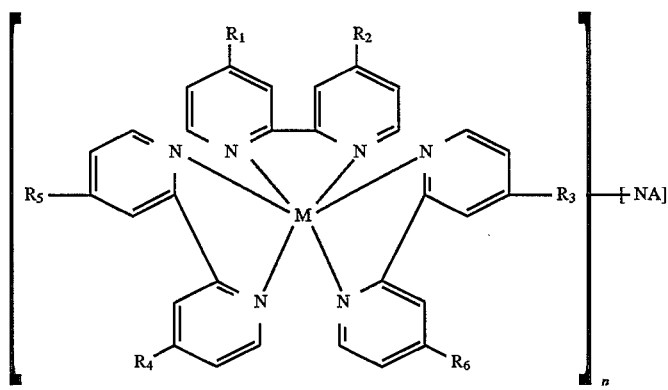

wherein M is ruthenium, osmium or rhenium, $R_1$, $R_2$, $R_3$, $R_4$, $R_5$ and $R_6$ may be the same or different and each is H, alkyl of 1–4 carbon atoms or a linker group, NA is said nucleic acid sequence linked to one of the bipyridyl groups at its 3' end or to two bipyridyl groups at its 3° and its 5' ends and n is either 1 or 2; (b) conducting a polymerase or other primer directed reaction; and (c) measuring the electrochemiluminescence of said labeled amplification product. In a particularly preferred embodiment, a multiple number of 3' labeled nucleic acid sequences are incorporated in a primer directed reaction.

EXAMPLES

Methodology

Oligonucleotides were synthesized on an Applied Biosystems 380B DNA synthesizer and functionalized with 5' or 3' amino groups using amino modifiers from Clontech (10). The oligonucleotides specific for the HIV gag gene PCR assays were the SK38 primer (ATAATCCACCTATCCCAGTAGGAGAAAT) (SEQ ID NO:3) the SK39 primer (TTTGGTCCTTGTCTTATGTCCAGAATGC) (SEQ ID NO:4) and the SK19 probe (ATCCTGGGATTAAATAAAATAGTAAGAATGTATAGC CCTAC) (SEQ ID NO:5) as previously described (6). Probe SK19 was labeled at both 3' and 5' ends using the tag-NHS. In the case of the cystic fibrosis gene the oligonucleotides were CFF(GACTTCACTTCTAATGATGA) (SEQ ID NO:6) and CFR(CTCTTCTAGTTGGCATGCT) (SEQ ID NO:7) for priming. The probes were CFN2 (GAAACACCAAAGATGATATT) (SEQ ID NO:8) for the normal gene and CFD2 (AACACCAATGATATTTTCTTT) (SEQ ID NO:9) for the 508 deletion. These were labeled at 3' and 3'5' sites via amino groups with the N-hydroxy succinimide ester of Ru(bpy)$_3^{2+}$ (8,9,11). Primers SK39 and CFF were the 5' biotinylated primers in the amplification reaction with unlabeled SK38 and CFR respectively. A non-specific oligonucleotide lambda 1 (GAAAATGTGCTGACCGGACATGAAAATGAG) (SEQ ID NO:10) was also synthesized and labeled at the 3' end to use as a control for background signals. Oligonucleotides were prepared for labeling by Biogel P6 column chromatography in 0.3M NaCl, followed by precipitation of the excluded oligonucleotide peak. Typically, 0.1 μmole of oligonucleotide was reacted with 0.5 μmole of ORIGEN™ (ruthenium ECL label) Label in 80% dimethyl sulfoxide/ phosphate buffered saline, pH 7.4. Biotinylation of the oligonucleotides was performed essentially as above except biotin X-NHS (Clontech) in 50% dimethyl sulfoxide was used for labeling. The labeled oligonucleotides were precipitated with ethanol and washed to remove unincorporated label. The synthetic cystic fibrosis sequences used to test the specificity of the system were as follows, the normal sequence, CF normal; GACTTCACTTCTAATGAT-GATAAAGAAAATATCATCTTTGGT-GTTTCCTATGATGAATATAGATACA-GAAGCGAGCATGCCAACTAGAAGAG (SEQ ID NO:11) and the mutant sequence, CF D508; GACTTCACT-TCTAATGATGATAAAGAAAATATCATTG-GTGTTTCCTATGATGAATATAGATACA-GAAGCGAGCATGCCAACTAGAAG AG (SEQ ID NO:12).

The PCR for the HIV1 gag gene was performed essentially as described (6) using a 25 μl reaction volume containing 75 ng (7.5 pmoles) of the biotinlylated SK39 and 75 ng (7.5 pmoles) of SK38 and 1.25 ng of SK19. The temperature cycles used on the Perkin Elmer Thermocycler were as follows: 95° C. 1 min., 60° C. 1 min., the cycle number was 40. This was followed by a cycle of 60° C. 30 min.

Polymerase chain reactions for the cystic fibrosis gene or synthetic genes were performed essentially as described (7) using 25 μl reaction volumes containing 75 ng (7.5 pmoles) of CFR and 75 ng (7.5 pmoles) of CFF biotinylated, and 5 ng of CFN2 or CFD2 labeled at the 3' or 3'5' ends. The cycle conditions for the cystic fibrosis assay were 30 cycles of 94° C. 1 min., 55° C. 2 min., 72° C. 2 min. This was followed by a cycle of 98° C. 5 min. 65° C. 30 min. The synthetic genes were used at concentration to mimic the concentration in normal human DNA for single copy genes i.e. $3 \times 10^5$ per µg of DNA. Salmon sperm DNA was used as a non specific DNA in these synthetic gene amplification reactions.

Following the PCR/hybridization cycles 2 µl samples were added to 15 µg of 2.8 µm streptavidin coated magnetic beads (Dynal, Great Neck, N.Y.) in 240 µl of ECL assay buffer on an ECL analyzer, incubated for 15 min. followed by analysis for ECL. In the case of the cystic fibrosis assay the samples were added to 240 µl of 30% formamide/ ORIGEN™ assay buffer.

EXAMPLE I

Assay Format For Rapid One Step Assay

The PCR reaction was run using a biotinylated primer and an unlabeled primer. The PCR thermocycles were run as normal for 40 cycles. At the end of the thermocycling an extended incubation was added for the hybridization. The samples at the end of the final incubation cycle were then ready for binding to beads, samples were taken and added to beads for binding (15 min.) at room temperature on an ECL analyzer, then analyzed for electrochemiluminescence. The results are shown in FIG. 1.

EXAMPLE II

Assay For HIV 1 gag, Rapid One Step Assay

The PCR was run for 35 cycles with the HIV1 gag specific primers including the SK19 3'5' labeled probe. The samples of positive HIV1 DNA were dilutions of the standard provided in the Perkin Elmer Cetus Kit. Samples of the PCR 2 µl were added to streptavidin beads incubated with shaking for 15 min. and analyzed for electrochemiluminescence using an ECL analyzer.

Figure 2:
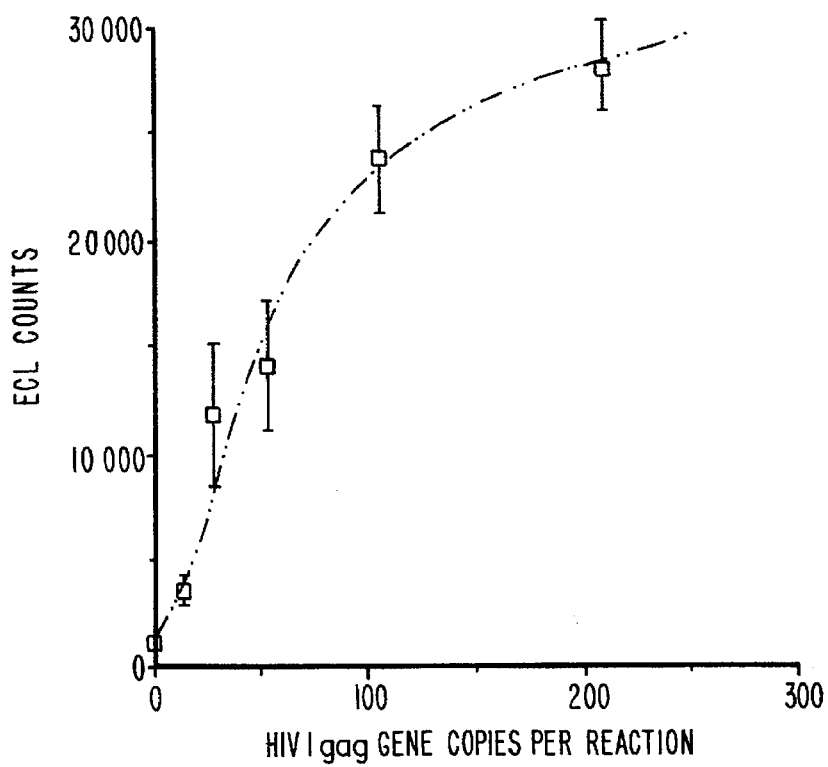
FIG. 2 is an assay for HIV 1 gag, rapid one step assay.

The results are shown in FIG. 2. FIG. 2 demonstrates a simplified PCR assay for rapid detection of the HIV1 gag gene. This ability is due in part to the ECL system and the ECL-based assay formats. The ECL system specifically provides (i) a stable label, able to withstand the rigors of the PCR, (ii) an assay modality which due to the nature of the ECL removes the need for external washes, (iii) a sensitivity for the detection of analyte which rivals radioactivity.

The results for the HIV1 gag study demonstrated the detection of copy numbers down to 12.5 copies with little effort. The utility of this methodology for a rapid screening system is clear and would, with improved thermocycler performance, allow the detection of much lower copy numbers.

EXAMPLE III

Assay For The Cystic Fibrosis Gene, Rapid One Step Assay

The assay of the invention was used to discriminate genes which had few mutations compared to the normal gene as is the case for the 508 codon deletion in the cystic fibrosis gene. The assay was tested using human DNA from cell lines, from human placenta, from normal subjects and with synthetic genes.

The PCR was run for 30 cycles with the cystic fibrosis specific primers including the 3'5' labeled CFN2. The samples of DNA were dilutions of DNA isolated from a human cell line (HeLa,8). Samples of the PCR 2 µl were added to streptavidin beads incubated with shaking for 15 min. and analyzed for electrochemiluminescence using an ECL analyzer.

Figure 3:
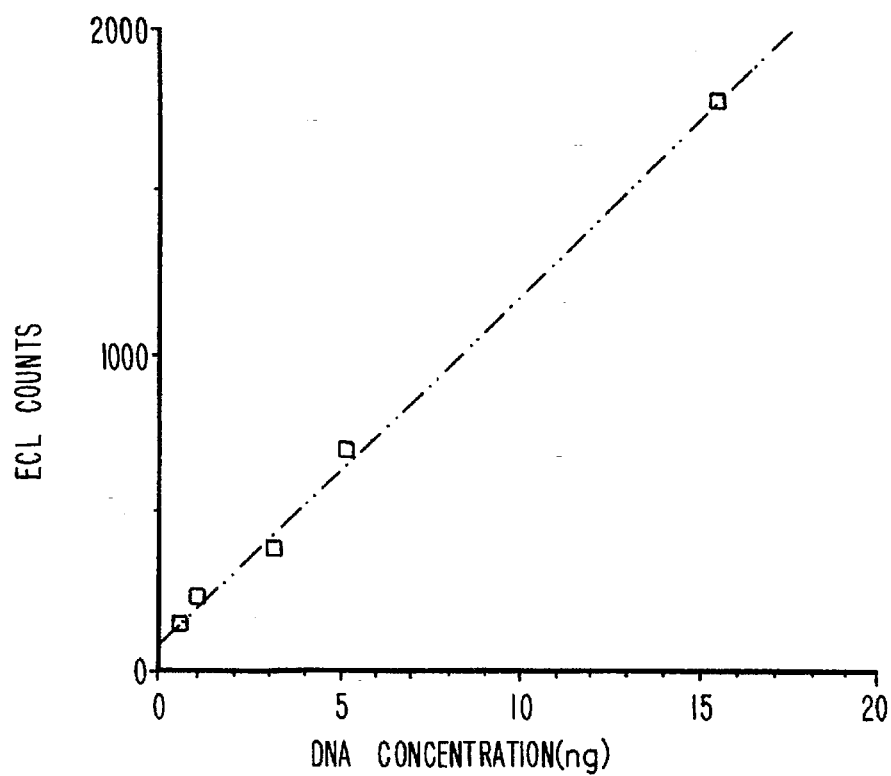
FIG. 3 is an assay for the cystic fibrosis gene, rapid one step assay.

The results of the assay are illustrated in FIG. 3. The success of the assay for the cystic fibrosis gene and as expected the sensitivity of the system enabling the detection of the gene in less than 1 ng of human DNA is demonstrated.

EXAMPLE IV

Assay for Synthetic Cystic Fibrosis Genes, Demonstrating it Specificity

To investigate the specificity of the invention for the cystic fibrosis gene two synthetic sequences were generated which contained, respectively, the normal gene sequence and the mutant gene sequence, containing the 508 deletion. These gene standards were diluted to the concentration found in human DNA to determine the specificity of the hybridization reaction without any doubt as to the nature of the cystic fibrosis sequences being amplified.

The PCR was run for 30 cycles with the cystic fibrosis specific primers including the 3' labeled probes CFN2 and CFD2. The samples of DNA were dilutions of synthetic DNA made into salmon sperm DNA. The concentration of these sequences was at the same level, as found in human DNA. Samples of the PCR 2 µl were added to 15 µg of streptavidin beads incubated with shaking for 15 min. and analyzed for electrochemiluminescence using an ECL analyzer.

Figure 4:
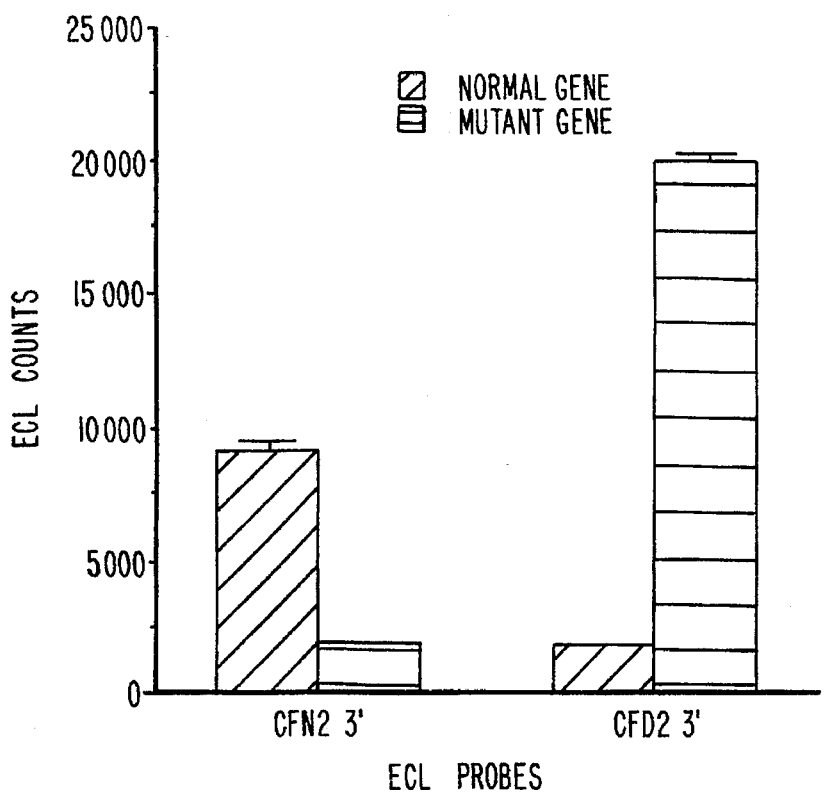
FIG. 4 is an assay for synthetic cystic fibrosis genes, demonstrating its specificity.
Figure 5:
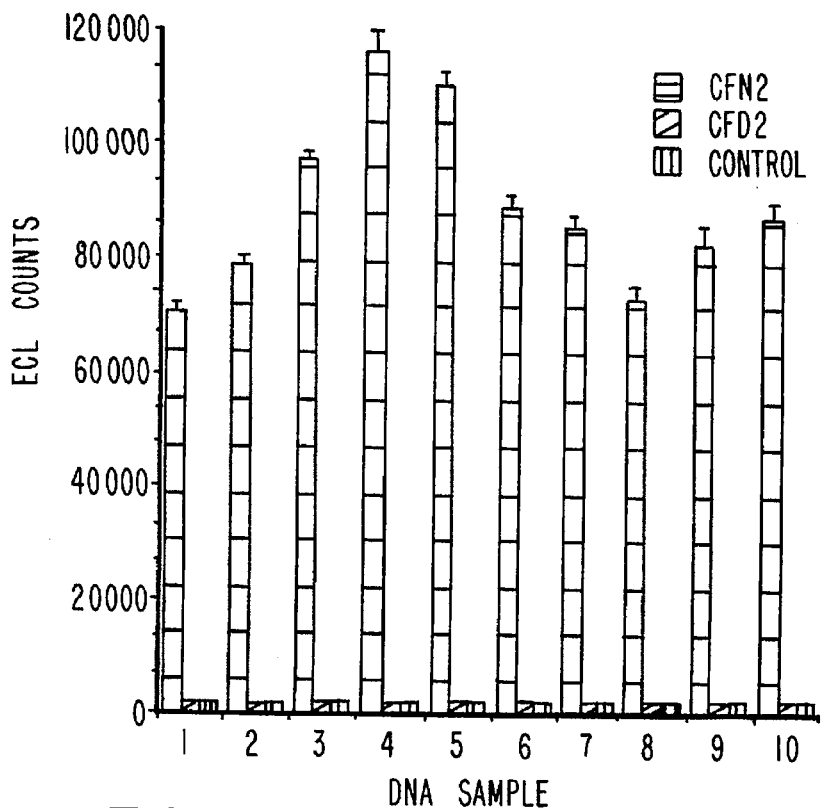
FIG. 5 is an assay for cystic fibrosis genes in normal human samples.

The results shown in FIG. 4 show the assay's ability to detect specifically the normal or the mutant gene. This rapid assay format is able to rapidly detect and discriminate closely related sequences.

EXAMPLE V

Assay for Cystic Fibrosis Genes in Normal Human Samples

The PCR was run for 30 cycles with the cystic fibrosis specific primers including the 3'5' labeled probes CFN2 and CFD2. The samples of DNA were individual samples of Human DNA isolated from individual chorionic membranes (Sigma Ltd). Samples of the PCR 2 µl were added to 15 µg of streptavidin beads incubated with shaking for 15 min. and analyzed for electrochemiluminescence using an ECL analyzer.

EXAMPLE VI

Figure 6:
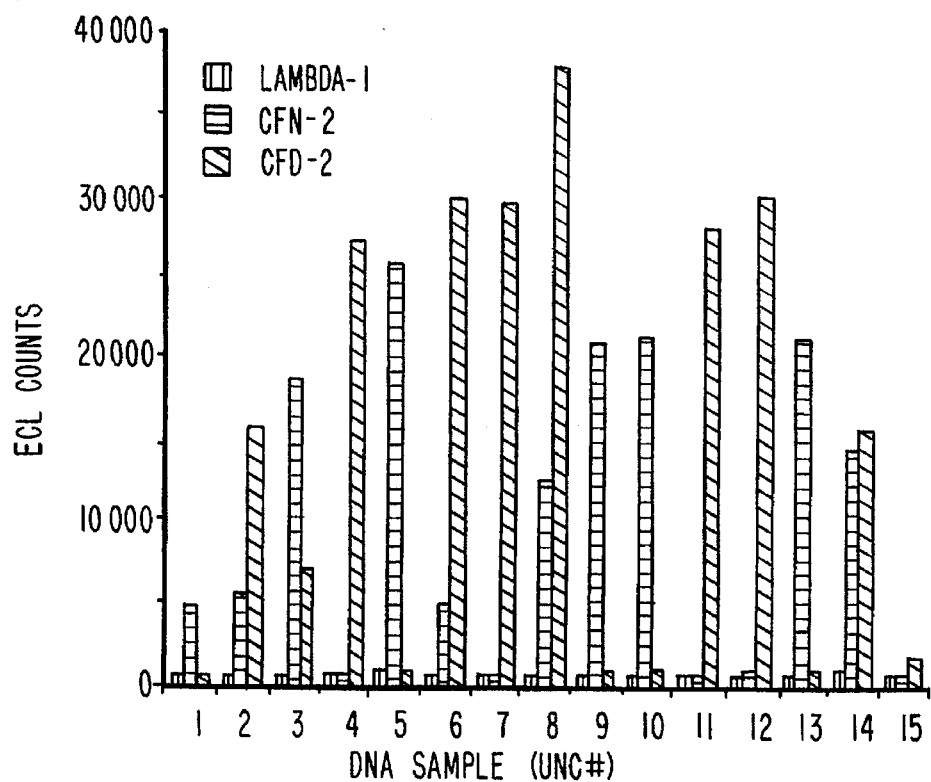
FIG. 6 is an assay for cystic fibrosis genes in human samples from the University of North Carolina.

Assay for Cystic Fibrosis Genes in Human Samples from University of North Carolina The data from Example IV was corroborated by assaying a set of human DNA samples from North Carolina where each of the samples was accurately assayed using the method of the invention compared to previous methods (7). The data exhibited a wide range of signals due to the vagaries of the PCR and the variation in the sample DNA concentration but with the consistence of the background it was possible to score the presence of the normal gene by the signal obtained with the CFN2 probe and the presence of the mutant gene with the CFD2 probe. Sample 15 in these studies gave the lowest signal but still significantly above the non-specific probes signal. The data are set forth in FIG. 6.

The PCR was run for 30 cycles with the cystic fibrosis specific primers including the 3' labeled probes CFN2, CFD2, and a non specific probe (lambda 1). The samples of DNA were individual samples of Human DNA at 0.5 to 2.5 µg/µl, 1 µl of each of these was used in the PCR. Samples of the PCR 2 μl were added to 15 μg of streptavidin beads incubated with shaking for 15 min. and analyzed for electrochemiluminescence using an ECL analyzer.

REFERENCES

1. Newman, A. R., Analytical Chemistry 1990; 62:1063A–065A.
2. Urdea, M. S., et al., Nucleic Acids Res. 1988; 6:4937–56.
3. Arnold, L. J., et al., Clin. Chem. 1989; 35:1588–94.
4. Beck, S., et al., Nucleic Acids Res. 1989; 17:5115–123.
5. Mullis, K. B., U.S. Pat. Nos. 4,683,195 and 4,683,202.
6. Ou C.-Y., et al., Science 1988; 239:295–97.
7. Prior, T. W., et al., Clin. Chem. 1990; 36:1756–59.
8. Kenten, J. H., et al., Clin. Chem. 1991; 37:1626–32.
9. PCT published application number US87/00987 (WO87/06706).
10. Nelson, P., et al., Nucleic Acids Res. 1989; 7:7187.
11. Blackburn, G. F., et al., Clin. Chem. 1991; 37:1534–39.

---

What is claimed is:

1. A method of determining the presence or amount of a nucleic acid sequence of interest in the amplification product of a polymerase chain reaction or other primer-initiated, template-directed reaction comprising the steps of:

(a) including in a polymerase chain reaction mixture or other primer-initiated, template-directed reaction mixture at least one labeled nucleic acid sequence complementary to said nucleic acid sequence of interest labeled (i) at the 3' end thereof, or (ii) at the 3' and the 5' end thereof with an electrochemiluminescent compound;

(b) conducting a polymerase chain reaction or other primer-initiated, template-directed reaction wherein an amplification product is formed, and thereafter labelling said amplification product with said labeled nucleic acid sequence, thereby forming a labeled amplification product; and (c) detecting the electrochemiluminescence of labeled amplification product such that the presence or amount of the nucleic acid sequence of interest can be determined.

2. A method as recited in claim 1 wherein a plurality of the 3' labeled nucleic acid sequence is included in a primer-initiated, template-directed reaction.

3. A method of determining the presence or amount of a nucleic acid sequence of interest in the amplification product of a polymerase chain reaction or other primer-initiated, template-directed reaction comprising the steps of:

(a) including in a polymerase chain reaction mixture or other primer-initiated, template-directed reaction mixture at least one labeled nucleic acid sequence complementary to said nucleic acid sequence of interest and labeled (i) at the 3' end thereof, or (ii) at the 3' and the 5' end thereof with an electrochemiluminescent compound of the formula:

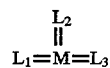

wherein M is selected from the group consisting of Ru, Os and Re and $L_1$, $L_2$ and $L_3$ are the same or not all the same and each is

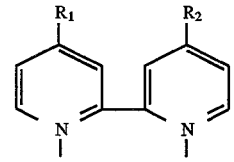

wherein $R_1$ and $R_2$ are the same or different and each is H, an alkyl group of 1–4 carbon atoms or a linker to said nucleic acid;

(b) conducting a polymerase chain reaction or other primer-initiated, template-directed reaction wherein an amplification product is formed, and thereafter labelling said amplification product with said labeled nucleic acid sequence, thereby forming a labeled amplification product; and (c) detecting the electrochemiluminescence of labeled amplification product such that the presence or amount of the nucleic acid sequence of interest can be determined.

4. A method of determining the presence or amount of a nucleic acid sequence of interest in the amplification product of a polymerase chain reaction or other primer-initiated, template-directed reaction comprising the steps of:

(a) including in a polymerase chain reaction mixture or other primer-initiated, template-directed reaction mixture at least one labeled nucleic acid sequence complementary to said nucleic acid sequence of interest labeled (i) at the 3' end thereof, or (ii) at the 3' and the 5' end thereof with an electrochemiluminescent compound;

(b) conducting a polymerase chain reaction or other primer-initiated, template-directed reaction wherein an amplification product is formed, and thereafter labelling said amplification product with said labeled nucleic acid sequence, thereby forming a labeled amplification product;

(c) concentrating and washing the labeled amplification product; and (d) detecting the electrochemiluminescence of labeled amplification product such that the presence or amount of the nucleic acid sequence of interest can be determined.

5. A method as defined in claim 1, wherein the labelling of said amplification product comprises hybridizing the labeled nucleic acid sequence to said amplification product.

6. A method as defined in claim 1, wherein the amplification product is not separated from the polymerase chain reaction mixture prior to said labelling.

7. A method of determining the presence or amount of a nucleic acid sequence of interest in the amplification product of a polymerase chain reaction or other primer-initiated, template-directed reaction comprising the steps of:

(a) including in said polymerase chain reaction mixture or other primer-initiated, template-directed reaction mixture at least one electrochemiluminescent moiety-labeled nucleic acid sequence complementary to said nucleic acid sequence of interest of the formula:

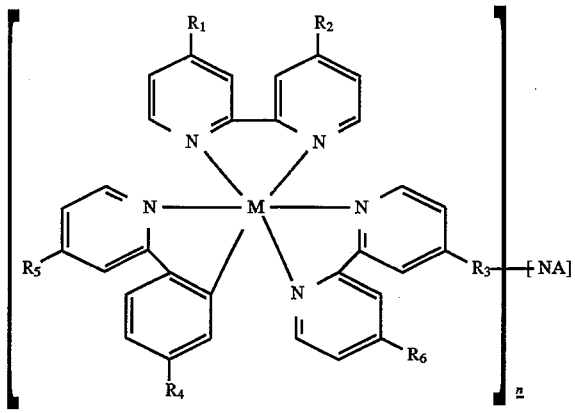

wherein M is ruthenium, osmium or rhenium, $R_1$, $R_2$, $R_3$, $R_4$, $R_5$ and $R_6$ may be the same or different and each is H, alkyl of 1–4 carbon atoms, or a linker to NA, NA is said nucleic acid sequence linked through a linker to one of $R_1$, $R_2$, $R_3$, $R_4$, $R_5$ and $R_6$ or directly to one of the bipyridyl groups at its end or to one of the $R_1$, $R_2$, $R_3$, $R_4$, $R_5$ and $R_6$, or directly to one of the bipyridyl groups at each end of its 3' and its 5' ends, said linker having at least one carbon atom and n is either 1 or 2;

(b) conducting a polymerase chain reaction or other primer-initiated, template-directed reaction wherein an amplification product is formed, and thereafter labelling said amplification product with said electrochemiluminescent moiety labeled nucleic acid sequence, thereby forming a labeled amplification product; and (c) detecting the electrochemiluminescence of labeled amplification product such that the presence or amount of the nucleic acid of interest can be determined.

* * * * *